United States Patent [19]

Rohr et al.

[11] Patent Number: 4,766,002
[45] Date of Patent: Aug. 23, 1988

[54] FLAVORING WITH α-CAMPHOLENIC ALCOHOL

[75] Inventors: Martin Rohr, Glen Rock; Richard H. Potter, Hasbrouck Heights; Richard E. Naipawer, Wallington, all of N.J.

[73] Assignee: Givaudan Corporation, Clifton, N.J.

[21] Appl. No.: 829,635

[22] Filed: Feb. 13, 1986

Related U.S. Application Data

[63] Continuation of Ser. No. 466,820, Feb. 16, 1983, abandoned.

[51] Int. Cl.⁴ .............................................. A23L 1/235
[52] U.S. Cl. .................................... 426/538; 560/231; 568/838
[58] Field of Search .................. 426/538; 560/231; 568/838

[56] References Cited

U.S. PATENT DOCUMENTS

| | | |
|---|---|---|
| 3,632,633 | 1/1972 | Louvar . |
| 3,978,009 | 8/1976 | Schulte . |
| 4,052,341 | 10/1977 | Naipawer et al. ............... 568/838 X |
| 4,278,569 | 7/1981 | Yoshida et al. .................. 252/522 R |

FOREIGN PATENT DOCUMENTS

| | | |
|---|---|---|
| 2330666 | 6/1977 | France . |
| 2335244 | 7/1977 | France . |
| 68936 | 9/1969 | German Democratic Rep. . |
| 0035041 | 3/1980 | Japan ..................................... 426/538 |
| 2024208 | 1/1980 | United Kingdom . |

OTHER PUBLICATIONS

A. F. Thomas, Helvetica Chimica Acta 55, 815 (1972).
Derwent Abstracts 72394, Abstracting Japan Patent 511426 of 2/22/79.

*Primary Examiner*—Joseph Golian
*Attorney, Agent, or Firm*—Robert F. Tavares; Linda A. Vag

[57] ABSTRACT

Compounds of the general formula

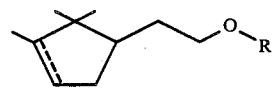

wherein R is hydrogen or an acyl group of two to five carbon atoms and the dotted line is an optional bond, are valuable flavor compounds and can be used to improve the flavor of foodstuffs and luxury consumables.

16 Claims, No Drawings

FLAVORING WITH α-CAMPHOLENIC ALCOHOL

This application is a continuation of application Ser. No. 466,820 filed Feb. 16, 1983 now abandoned.

INTRODUCTION

The art of creating flavors involves blending a number of substances having individual characteristics to produce a composition which has the desired flavor. A successful product is not simply a combination of pleasant tasting materials; a successful product is one in which the individual character of each of the components is not readily perceived per se, but blends with each of the other flavor notes to provide a single organoleptic impression.

To create this single organoleptic impression, the flavorist uses a number of compounds which not only contribute their own characteristic flavor to the blend, but which tie together the other materials used in the composition to form a more uniformly blended composition. To meet the demands of the flavorist, such a chemical must not only tie together the individual contributions of the other materials, but must do it in such a way that the resulting flavor more closely resembles the natural flavor. This latter ability is described by the flavorist as the ability to add "naturalness" to the composition. There is always a need for compounds which have this ability.

THE INVENTION

The present invention concerns flavor compositions, foodstuffs and luxury consumables (tobacco, chewing gum, etc.) wherein the flavor has been improved, enhanced or modified by the addition of a compound of the formula

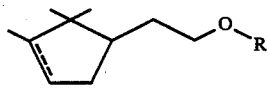   I wherein R is hydrogen or an acyl group of from two to five carbon atoms and the dotted line represents an optional bond.

The compounds of formula I are characterized by organoleptic properties that make them especially useful in flavor compositions. Although several of the compounds represented by formula I are known, there is no mention of their organoleptic properties in the prior art.

The compound of formula I wherein R is hydrogen and the dotted line represents an additional bond is known as 2-(2,2,3-trimethylcyclopent-3-en-1-yl)ethanol, or more commonly as α-campholenic alcohol. The compounds used in this invention will be referred to as derivatives of α-campholenic alcohol.

The compounds of formula I wherein R is hydrogen or acetyl are known; those wherein R is an acyl group of from three to five carbon atoms are novel.

DESCRIPTION OF THE PREFERRED EMBODIMENTS

The alcohols and esters used in this invention may be conveniently prepared by synthetic methods which are generally known in the art. The α-campholenic alcohol for example, may be prepared by a metal hydride reduction of α-campholenic aldehyde. Both the (R)- and (S)-alcohols were made by reducing the corresponding (R)-and (S)-α-campholenic aldehydes prepared in accord with the procedures described in U.S. Pat. No. 4,052,341. No perceptible differences were noted in the flavors of the two antipodes and the (R)-isomer, the (S)-isomer or enantiomeric mixtures can be used interchangeably.

Dihydro-α-campholenic alcohol can be prepared from the α-campholenic alcohol by hydrogenation of the double bond, from the dihydro-α-campholenic aldehyde by reduction of the carbonyl group, or from α-campholenic aldehyde by reduction of the carbon-carbon double bond and carbonyl group simultaneously. All three approches are within the ordinary skill of a chemist. The process employed herein is the hydrogenation of α-campholenic alcohol using a metal catalyst (e.g. 5% palladium on carbon).

The esters of α-campholenic alcohol and dihydro-α-campholenic alcohol may be prepared by general esterification methods known in the art for producing esters of primary alcohols. Suitable methods are provided in the examples.

The compounds of formula I may be mixed with other flavoring materials to prepare flavor compositions which can be used to improve, enhance or modify the flavor of foodstuffs, or luxury consumables (e.g. tobacco products). The compounds could be added directly to said foodstuffs and luxury consumables, but it is normally the practice of the art to prepare a flavor mixture which is then added to the final product. Such foodstuffs and luxury consumables include, but are not limited to, gums, candies, jellies, gelatins, soft drinks (carbonated and noncarbonated), desserts, liquors, yogurts, teas, tobaccos, tobacco products and the like.

The compounds of formula I have properties which make them useful for improving, enhancing or modifying the organoleptic impression of flavor compositions, foodstuffs and luxury consumables. Although each of the compounds of formula I has its own unique and characteristic flavor, all of these compounds can be described as fruity and are preferably used to improve, enhance or modify the fruity character of a flavor. The α-campholenic alcohol is of foremost preference because it is distinctly superior to the other compounds and has an outstanding ability to provide "naturalness" to flavors. Next in preference is the dihydro-α-campholenic alcohol which is somewhat similar to the α-campholenic alcohol although slightly weaker in strength.

The esters of formula I all have flavors which are of a general fruity character with distinguishable berry notes and, in some instances, with floral topnotes. They are generally useful for imparting fruity notes and for enhancing the "naturalness" of a fruity flavor. The compound 2-(2,2,3-trimethylcyclopentan-1-yl)ethyl 2-methylpropionate possesses a natural fruit flavor and strong berry-like notes and is the preferred ester of formula I.

The alcohols of formula I, the especially preferred compounds of this invention, are characterized by particularly well defined sweet, natural, specific berry-like notes. Camphoraceous middle notes and woody backnotes also make important contributions to the flavor character of these compounds. These alcohols have a unique ability to improve or enhance the natural quality of fruity notes in general and are particularly valuable for the natural berry notes they can contribute. Because of these unique berry notes, the alcohols find special application in formulating berry flavors, especially strawberry, raspberry and black raspberry. These alcohols have also been found to be particularly useful in citrus flavors wherein they contribute a juicy top note to the flavor, i.e. make it taste more natural and more reminiscent of the natural juice flavor. As noted previously, of the two alcohols, α-campholenic alcohol is the somewhat stronger flavorant and is especially preferred for that reason.

A number of examples are provided herein to illustrate the utility of the compounds of this invention in fruit flavors. For example, when the α-campholenic alcohol was used in a raspberry flavor, the flavor was found to be rounder, more uniformly blended, more berry-like and more reminiscent of the taste of the natural berries. Similar effects were found when the compound was used in a strawberry flavor. When α-campholenic alcohol was incorporated into an orange flavor, the flavor with the compound present was considered to be better blended, rounder and more reminiscent of the natural fruit than the flavor without the compound. The flavor containing the compound was considered "more juicy", i.e. gave an impression more reminiscent of the natural orange juice.

The compounds of formula I are also particularly useful for improving the organoleptic properties of tobacco and tobacco products, e.g. tobaccos themselves, tobacco by-products such as reconstituted and homogenized leaf and stem, tobacco surrogates such as lettuce and cabbage leaf, materials used in tobacco processing such as paper filters, etc. and flavoring substance compositions used for tobacco products.

The use of α-campholenic alcohol is illustrated in the examples by its incorporation into a tobacco blend consisting of bright and burly tobaccos, stems and reconstituted leaf. When the treated cigarettes were compared with untreated cigarettes the former were found to smoke smoother and provide a more pleasant taste. The addition of the compound enhanced the "fullness" of the smoke and the feeling of moistness in the mouth.

When preparing flavor compositions, the compounds of formula I are preferably used in the range of 0.5% to 20% by weight of the flavor imparting ingredients with 2% to 10% being especially preferred. In the finished foodstuff to be flavored, the compounds of formula I are preferably present at a level of about 0.1 ppm to 200 ppm with 1 ppm to 30 ppm being especially preferred. In the flavoring of tobacco products, the preferred range would be between 100 ppm to 250 ppm of the tobacco or tobacco surrogate used with 175 ppm to 225 ppm being especially preferred. While the above are the preferred amounts contemplated, it should be understood that the amount and manner of use are dependent on the skill and preference of the flavorist and that greater amounts could be used to create special effects.

The claims are to be understood as not encompassing the use of natural materials which may contain a compound of this invention along with many other compounds of said natural materials and which have not been processed for the purpose of increasing the concentration of a compound of this invention to a point where the processed material can be used as a substitute for said compound contained therein.

ILLUSTRATION OF THE PREFERRED EMBODIMENTS

The following examples are provided to illustrate the preferred embodiments as they are disclosed herein and are not to be construed as limiting.

Infrared spectra (ir) were recorded as neat samples on a Perkin-Elmer Model 457 spectrophotometer and absorptions are reported in inverse centimeters ($cm^{-1}$).

Molecular weights were determined on a Finnigan Model 4000 mass spectrometer.

Nuclear magnetic resonance (nmr) spectra were recorded as solutions in chloroform-$d_1$, using a Varian EM-360 proton spectrometer ($^1H$-nmr) and a Varian Model CFT-20 heteronuclear spectrometer ($^{13}C$-nmr), and are reported as $\delta$ units relative to tetramethylsilane (TMS) (0.0$\delta$).

Gas-liquid chromatography (glc) was carried out on a 10% Carbowax®—20M (6 ft.×¼ in.) column using a Varian Model 2700 gas chromatograph with thermal conductivity detector (TC).

Unless otherwise indicated weights are in grams, temperatures are in degrees centigrade, pressures are in mm Hg and yields are based on theory.

EXAMPLE I

This example illustrates the preparation of compounds of formula I.

A. Preparation of α-Campholenic Alcohol
[2-(2,2,3-Trimethylcyclopent-3-en-1-yl)ethanol]

1. To a stirred suspension of 76 g (2.0 moles) of sodium borohydride, 800 ml of ethanol, 200 ml of water and 15 ml of 30% aqueous sodium hydroxide solution was added 608 g (4.0 moles) of α-campholenic aldehyde (prepared according to U.S. Pat. No. 4,052,341 Example I) over 1.0 hour at 25°–35° C. The resultant mixture was stirred at room temperature for an additional 5.0 hours, and subsequently quenched by pouring it into a stirred mixture of 600 ml of water and 25 ml of 30% aqueous sodium hydroxide solution. The mixture was allowed to settle and the lower aqueous layer was separated off and was extracted with two 200-ml portions of hexane. The oil layer and hexane extracts were combined and were washed with two 400-ml portions of water. The hexane layer was dried over anhydrous magnesium sulfate, filtered and the solvent was removed by atmospheric distillation.

The remaining oil was distilled at reduced pressure (0.6 mm Hg) to yield 544.1 g (88.3% yield) of α-campholenic alcohol: bp 72°–76° C. (0.5 mm); $n_D^{20}$ 1.4728; mol wt. 154 (ms); nmr ($^1H$) 0.8$\delta$ (3H,s), 1.0 (3H,s), 1.6 (3H, broad s, olefinic CH$_3$), 1.5–2.5 (5H, broad complex), 3.1 (1H, broad s, D$_2$O exchangable, hydroxyl H), 3.7 (2H, t, J∼7Hz), 5.3 (1H, broad multiplet, olefinic H); ir 3330 $cm^{-1}$ (—OH), 3035, 800, no carbonyl absorption in the 1650–1750 $cm^{-1}$ region; flavor: sweet, berry, camphoraceous, with woody backnote.

2. Using the procedure of U.S. Pat. No. 4,052,341 Example I, (−)-α-pinene [$(\alpha)_D^{20}$ −40°0′] was converted to (S)-α-campholenic aldehyde which was reduced using sodium borohydride to (S)-α-campholenic alcohol [$(\alpha)_{300}^{20}$ −47.41°].

In an identical fashion, (+)-α-pinene [$(\alpha)_D^{20}$ +40°0′] was converted to (R)-α-campholenic aldehyde which was reduced to (R)-α-campholenic alcohol [$(\alpha)_{300}^{20}$ +47.42°].

A comparison of the ORD curves of the (R)-and (S)-aldehydes showed them to be mirror images as was the case with the (R)-and (S)-alcohols.

The flavor description of each isomer was similarly sweet, berry, camphoraceous.

B. Preparation of Esters of α-Campholenic Alcohol - General Procedure

A mixture of 46.2 g (0.30 mole) of α-campholenic alcohol, 75 ml of toluene, 0.1 g of p-toluenesulfonic acid monohydrate and 0.33 mole (10% excess) of the appropriate carboxylic acid was refluxed for 6.0 hours in a reaction flask (250-ml) equipped with a Dean-Stark water separator, during which time the theoretical amount of water was condensed from the distillate. The mixture was cooled and was poured into 100 ml of stirred 10% aqueous sodium carbonate solution. The upper toluene layer was separated and was washed with three 100-ml portions of water. The toluene was removed by distillation and the residual oil was purified by fractional distillation to give the following esters.

Acetate: 90.6% yield; bp 65°–70° C. (1.6 mm); mol wt 196 (ms); ir 1745 cm$^{-1}$ flavor fruity, berry, woody, floral backnote.

Propionate: 93.0% yield; bp 75°–77° C. (0.7 mm); mol wt 210 (ms); ir 1740 cm$^{-1}$; flavor: fruity, berry, slightly camphoraceous, green.

n-Butyrate: 89.7% yield; bp 80°–84° C. (0.6 mm); mol wt 224 (ms); ir 1740 cm$^{-1}$; flavor: floral, slightly fruity, camphoraceous, berry, slightly woody.

2-Methylpropionate: 88.4% yield; bp 77°–79° C. (0.5 mm); mol wt 224 (ms); ir 1735 cm$^{-1}$; flavor: fruity, slightly green, berry, woody backnote. The $^1$H and $^{13}$C-nmr data were consistent with the individual structures of each ester.

C. Preparation of Dihydro-α-campholenic Alcohol [2-(2,2,3-Trimethylcyclopentan-1-yl)ethanol]

A mixture of 77 g (0.5 mole) of α-campholenic alcohol, 1.54 g (2 wt-%) of dry 5% palladium on carbon and 75 ml of ethanol was hydrogenated at 26°–48° C. and 40–64 psi hydrogen pressure until hydrogen uptake ceased. The mixture was filtered to remove the catalyst and the solvent was removed from the filtrate by atmospheric distillation. The residual oil was fractionally distilled to yield dihydro-α-campholenic alcohol: 74.6 g (95.6% yield); bp 69°–74° C. (0.7 mm); mol wt 156 (ms); nmr ($^1$H) 0.5δ (3H,s), 0.9 (6H, overlapping s and d), 1.0–2.0 (8 H, broad complex), 3.1 (1H, broad s, D$_2$O exchangable, hydroxyl H), 3.6 (2H, broad multiplet, —CH$_2$OH) ; ir 3330 cm$^{-1}$(—OH), no olefinic absorptions at 3025 or 800 cm$^{-1}$; flavor: berry, slightly camphoraceous, sweet, slightly fruity.

D. Preparation of Esters of Dihydro-α-campholenic Alcohol - General Procedure A mixture of 39.0 g (0.25 mole) of dihydro-α-campholenic alcohol, 75 ml of toluene, 0.1 g of p-toluenesulfonic acid monohydrate and 0.30 mole (20% excess) of the appropriate carboxylic acid was refluxed for 5–6 hours in a reaction flask (250-ml) equipped with a Dean-Stark water separator, during which time the theoretical amount of water was condensed from the distillate. The mixture was cooled and was poured into 100 ml of stirred 10% aqueous sodium carbonate solution. The upper toluene layer was separated and was washed with three 100-ml portions of water. The toluene was removed by distillation and the residual oil was purified by fractional distillation to give the following esters.

Acetate: 92.3% yield; bp 72°–78° C. (0.9 mm); mol wt 198 (ms); ir 1745 cm$^1$; flavor: fruity, camphoraceous, prune-like.

2-Methylpropionate: 90.8% yield; bp 82°–83° C. (0.4 mm); mol wt 226 (ms); ir 1740 cm$^{-1}$; flavor: fruity, berry, with woody backnotes.

The $^1$H and $^{13}$C-nmr data were consistent with the individual structures of each ester.

Example II

This example illustrates the use of the compounds of the invention as flavorants.

A. Artificial Berry Flavors

| Constituents | Parts by Weight |
|---|---|
| 1. Raspberry Flavor | |
| α-Ionone | 2.85 |
| β-Ionone | 2.25 |
| Ethyl Acetate | 22.60 |
| Acetyl Methyl Carbinol (Acetoin) | 28.34 |
| delta-Decalactone | 2.25 |
| Linalool | 4.50 |
| α-Terpineol | 2.25 |
| cis-3-Hexen-1-ol | 2.25 |
| n-Amyl Alcohol | 4.50 |
| Caproic Acid | 18.07 |
| Caprylic Acid | 4.50 |
|  | 94.36 |
| α-Campholenic Alcohol | 5.64 |
| Total | 100.00 |
| 2. Strawberry Flavor | |
| Acetic Acid | 14.37 |
| Ethyl Methylphenylglycidate | 0.85 |
| Caprylic Acid | 2.85 |
| Diacetyl (Butanedione) | 0.57 |
| Ethyl Acetate | 26.00 |
| Ethyl Butyrate | 11.40 |
| gamma-Undecalactone | 1.40 |
| cis-3-Hexen-1-ol | 1.14 |
| Maltol | 7.14 |
| Levulinic Acid | 20.00 |
| Methyl 2-Methylbutyrate | 7.14 |
|  | 92.86 |
| α-Campholenic Alcohol | 7.14 |
| Total | 100.00 |

Both of the above artificial berry flavors were prepared with and without α-campholenic alcohol as indicated. In each case, the presence of the α-campholenic alcohol made a significant difference. The flavor of the composition was rounded out, more berry-like and more reminiscent of a natural fruit flavor.

B. Artificial Orange Flavor

| Constituents | Parts By Weight |
|---|---|
| Acetaldehyde | 1.0 |
| Ethyl Butyrate | 1.0 |
| Decanal | 0.4 |
| Linalool | 0.5 |
| Orange Oil Fl. C.P. | 95.1 |
|  | 98.0 |
| α-Campholenic Alcohol | 2.0 |
| Total | 100.0 |

The addition of α-campholenic alcohol to the above artificial orange flavor resulted in an improved composition. The presence of the alcohol increased the juiciness, rounded out the flavor and added to the natural notes.

Effects similar to those noted above for the addition of α-campholenic alcohol to flavor compositions can also be achieved with the use of dihydro-α-campholenic alcohol with perhaps an adjustment of the amount used.

C. Tobacco Product

A standard cigarette blend was prepared as described below:

| Constituent | Parts By Weight |
| --- | --- |
| Bright Tobacco | 55 |
| Burley Tobacco | 25 |
| Expanded Stems | 5 |
| Reconstituted Leaf | 15 |
| Total | 100 |

α-Campholenic alcohol (200 ppm by weight) was added to a portion of the blend and cigarettes were prepared with and without the additive and compared by smoking. The cigarettes containing the additive were markedly improved over those without it. The smoke was considerably smoother and more pleasant. The moistness of the mouth was markedly increased and the mouth feel or "fullness" of the smoke was enhanced.

We claim:

1. An improved flavor composition of the type used to impart a fruity flavor to a foodstuff wherein the improvement comprises the incorporation of 0.5% to 20% by weight of a substantially pure compound of the formula

wherein the dotted line represents an optional bond.

2. A composition according to claim 1 wherein the compound is 2-(2,2,3-trimethylcyclopent-3-en-1-yl)ethanol.

3. A composition according to claim 1 wherein the compound is 2-(2,2,3-trimethylcyclopentan-1-yl)ethanol.

4. A composition according to claims 2 or 3 wherein the amount of the compound incorporated is 2% to 10% by weight.

5. An improved foodstuff of the type having a fruity flavor wherein the improvement comprises the incorporation of 0.1 ppm to 200 pppm of a substantially pure compound of the formula

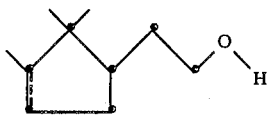

wherein the dotted line represents an optional bond.

6. A foodstuff according to claim 5 wherein the compound is 2-(2,2,3-trimethylcyclopent-3-en-1-yl)ethanol.

7. A foodstuff according to claim 5 wherein the compound is 2-(2,2,3-trimethylcyclopentan-1-yl)ethanol.

8. A foodstuff to claims 7 wherein the amount of the compound incorporated is 1.0 ppm to 30 ppm.

9. A method for improving the flavor of a flavor composition of the type used to impart a fruity flavor to a foodstuff which comprises incorporating therein 0.5% to 20% by weight of a substantially pure compound of the formula

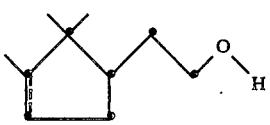

wherein the dotted line represents an optional bond.

10. The method of claim 9 wherein the compound is 2-(2,2,3-trimethylcyclopent-3-en-1-yl)ethanol.

11. The method of claim 9 wherein the compound is 2-(2,2,3-trimethylcyclopentan-1-yl)ethanol.

12. The method of claims 10 or 11 wherein the amount of the compound incorporated is 2% to 10% by weight.

13. A method for improving the flavor of a foodstuff of the type having a fruity flavor which comprises incorporating therein 0.1 ppm to 200 ppm of a substantially pure compound of the formula

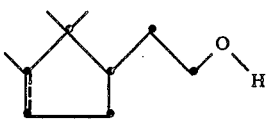

wherein the dotted line represents an optional bond.

14. The method of claim 13 wherein the compound is 2-(2,2,3-trimethylcyclopent-3-en-1-yl)ethanol.

15. The method of claim 13 wherein the compound is 2-(2,2,3-trimethylcyclopentan-1-yl)ethanol.

16. The method of claims 14 or 15 wherein the amount of the compound incorporated is 1 ppm to 30 ppm of the foodstuff.

* * * * *

UNITED STATES PATENT AND TRADEMARK OFFICE
CERTIFICATE OF CORRECTION

PATENT NO. : 4,766,002
DATED : August 23, 1988
INVENTOR(S) : Martin Rohr et al.

It is certified that error appears in the above-identified patent and that said Letters Patent is hereby corrected as shown below:

```
Delete "[1]" from the following claims:
claim 1, column 7, line 34
claim 5, column 8, line 2
claim 9, column 8, line 22
claim 13, column 8, line 41.

In claim 8, column 8, line 13, change "claims 7" to read
 -- claims 6 or 7 --.
```

On the title page, section [56], <u>References Cited</u>, under OTHER PUBLICATIONS, add -- Steffen Arctander "Perfume and Flavor Materials of Natural Origin", 1960, Elizabeth, New Jersey, pages 316-320. --

In the Specification, at column 5, line 18, correct "ir 1745 $cm^{-1}$ flavor fruity, berry, "to read -- ir 1745 $cm^{-1}$; flavor: fruity, berry, -- .

Column 3, line 33, "burly tobaccos" to read --burley tobaccos--.

Signed and Sealed this

Fourth Day of April, 1989

Attest:

DONALD J. QUIGG

*Attesting Officer*        *Commissioner of Patents and Trademarks*